United States Patent
Rapold et al.

(10) Patent No.: US 6,861,522 B2
(45) Date of Patent: Mar. 1, 2005

(54) PROCESS FOR THE MANUFACTURE OF THIAZOLE DERIVATIVES WITH PESTICIDAL ACTIVITY

(75) Inventors: Thomas Rapold, Muenchwilen (CH); Gottfried Seifert, Muenchwilen (CH); Marcel Senn, Schweizerhalle (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/415,259

(22) PCT Filed: Oct. 25, 2001

(86) PCT No.: PCT/EP01/12370

§ 371 (c)(1),
(2), (4) Date: Sep. 17, 2003

(87) PCT Pub. No.: WO02/34734

PCT Pub. Date: May 2, 2002

(65) Prior Publication Data

US 2004/0054189 A1 Mar. 18, 2004

(30) Foreign Application Priority Data

Oct. 27, 2000 (CH) .............................. 2105/00

(51) Int. Cl.⁷ ............................................ C07D 277/32
(52) U.S. Cl. ...................... 544/67; 548/202; 548/205
(58) Field of Search ................ 548/202, 205; 544/67

(56) References Cited

U.S. PATENT DOCUMENTS 5,180,833 A * 1/1993 Uneme et al. .............. 548/202
5,852,012 A * 12/1998 Maienfisch et al. ....... 514/229.2
6,214,998 B1 * 4/2001 Decker ....................... 548/202

FOREIGN PATENT DOCUMENTS

EP    0580553    1/1994
EP    1031566    8/2000

* cited by examiner

*Primary Examiner*—Laura L. Stockton
(74) *Attorney, Agent, or Firm*—Rose M. Allen

(57) ABSTRACT

A process for the preparation of a compound of the formula

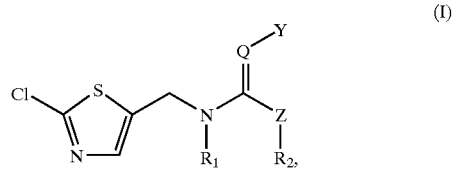

(I)

in which Q is CH or N; Y is $NO_2$ or CN; Z is $CHR_3$, O, $NR_3$ or S;

$R_1$ and $R_2$ are, for example, together an alkylene bridge which optionally contains an O; $R_3$ is H or unsubstituted or $R_4$-substituted $C_1$–$C_{12}$alkyl, $R_4$ is unsubstituted or substituted aryl or heteroaryl; wherein said compound has pesticidal activity.

4 Claims, No Drawings

PROCESS FOR THE MANUFACTURE OF THIAZOLE DERIVATIVES WITH PESTICIDAL ACTIVITY

This application is a 371 filing of International Application No. PCT/EP01/12370, filed Oct. 25, 2001, the contents of which are incorporated herein by reference.

The invention relates to a process for the preparation of a compound of the formula

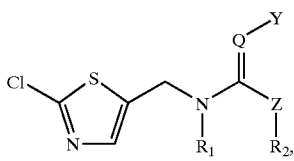

(I)

and optionally its E/Z-isomers, E/Z-isomer mixtures and/or tautomers, in each case in free form or in salt form, in which Q is CH or N;
Y is $NO_2$ or CN;
z is $CHR_3$, O, $NR_3$ or S;
$R_1$ and $R_2$ are either, independently of one another, hydrogen, unsubstituted or $R_4$-substituted $C_1$–$C_8$alkyl, or together are an alkylene bridge having two or three carbon atoms which optionally comprises a heteroatom chosen from the group consisting of $NR_5$, O and S,
$R_3$ is H or unsubstituted or $R_4$-substituted $C_1$–$C_{12}$alkyl,
$R_4$ is unsubstituted or substituted aryl or heteroaryl, and
$R_5$ is H or $C_1$–$C_{12}$alkyl; in which a) a compound of the formula

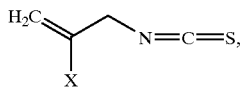

(II)

which is known or can be prepared by known methods, and in which X is a leaving group, is reacted with a halogenating agent to give a compound of the formula

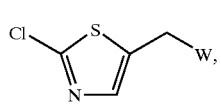

(III)

in which W is a halogen atom, or optionally a tautomer, in each case in free form or in salt form; and b) the resulting compound of the formula (III) is reacted with a compound of the formula

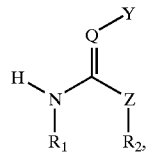

(IV)

which is known or can be prepared by methods known per se, and in which $R_1$, $R_2$, Y, Z and Q have the meanings given above for the compound of the formula (I);

wherein the preparation of the compound of the formula (III) according to process stage a) involves a purification step in which the crude product which has formed is treated with water in the acidic pH range;

to a process for the preparation of a compound of the formula (III) according to the above process a), and to the use of the compounds of the formulae (II), (III) and (IV) in a process as detailed above.

The compounds of the formula (I) are known as valuable pesticides, and methods for their preparation are described in the literature. In particular, various processes for the preparation of the key compound of the formula (III) are described. However, it has been found that considerable problems with regard to the purity of the compounds of the above formula (III) and also the pesticidally active, compounds of the formula (I) resulting therefrom arise with these preparation processes known from the literature. The byproducts of t he compounds of the formula (III) can only be separated off by distillation with large product losses and by means of complex, time-consuming measures. They severely impair the thermal stability of the compounds of the formula (III), which leads to considerable problems and long cycle times in a production operation. Furthermore, the increased purity of the compounds of the formula (III) also have a positive effect on the yield achieved in the subsequent stage. The known processes likewise have considerable disadvantages with regard to other parameters such as, for example, yield, storage stability of the compound of the formula (III), duration of the synthesis cycle, volume yield, disposal of waste materials which are problematical from an ecological and toxicological viewpoint, recycling of unreacted starting materials and the like. There is therefore the need to provide improved processes for the preparation of the compounds of the formula (I) and, in particular, of the formula (III).

To purify the compounds of the formula (III), various methods are proposed in the literature, such as, for example, the formation of the hydrochloride of the compound (III) in an organic solvent, subsequent filtration and subsequent liberation of the compound, for example by adding a base; purifying the crude compound of the formula (III) by crystallization from a suitable solvent; purification by evaporation of the organic product subsequent fractional distillation at reduced pressure; washing out of the organic product phase with a large amount of aqueous base; or else washing out of the solid organic product phase with a large amount of water.

These methods have the disadvantage that they often lead to a relatively low yield of compound of the formula (III) and that the quality thereof is inadequate for use in the subsequent stage. For example, during the fractional distillation, secondary components with a boiling behaviour similar to the compounds of the formula (III) cannot be separated off. If the reaction mass is brought into contact with a large amount of water at a high pH, it is possible for undesired hydrolysis products to arise, which in turn leads to a considerable loss in yield. In addition, it has, in particular, been found that the authorities' stipulations with regard to the pesticidally active compound of the formula (I) cannot be observed; even in cases of high yields and good quality during the preparation of the compounds of the formula (III), the use of the hitherto known purification processes of the compounds (III) gives, in the subsequent stage, compounds of the formula (I) which have a very marked brown coloration and form with comparatively poor yields. Surprisingly, it has now been found that the criterion that the appearance of the product must be pure white to beige can be directly satisfied with the purification process of the compound of the formula (III) claimed according to the invention.

The abovementioned byproducts which are difficult to separate off are, inter alia, the compounds of the formulae

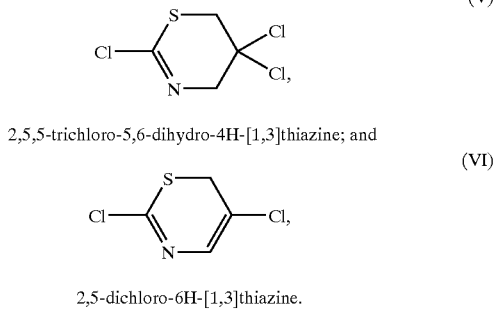

2,5,5-trichloro-5,6-dihydro-4H-[1,3]thiazine; and (VI)

2,5-dichloro-6H-[1,3]thiazine.

The compound of the formula (V) is usually the most important byproduct produced during the preparation of the compounds of the formula (III). It is often formed in amounts of 6–10% by weight based on the compound of the formula (III). It has been found that the compounds of the formula (V) and (VI) can only be separated off inadequately even via distillation over a multitray or fractionating column. They inferfere with the synthesis of the compounds of the formula (III) and reduce the yield and quality thereof.

Surprisingly, we have now found a simple method by which the byproducts which form during the preparation of the compounds of the formula (III) can be separated off relatively easily. The procedure consists essentially in bringing the reaction mass, which comprises the compound of the formula (III) and possibly unreacted compound of the formula

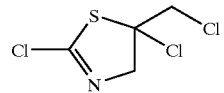

into contact with water in the acidic pH range, and then isolating the desired compound of the formula (III) in a suitable manner. For this, either aqueous acid or simply water is added to the acidic reaction mass. Two particular embodiments are of particular interest here. Either a1): the reaction mass is treated, following the synthesis of the compound of the formula (III), with aqueous acid, preferably concentrated hydrochloric acid. Particularly when the solvents used are water-soluble, this is advantageously carried out following evaporation of some or else all of the solvent. The compound of the formula (III) is transferred from the reaction mixture which forms as hydrochloride salt into the acidic aqueous phase. The readily hydrolysable byproducts are destroyed, but not the desired product. In this purification process, the product is then recovered by, for example, increasing the pH of the aqueous product phase, for example by diluting with water or by adding some base, and taking up the liberated compound of the formula (III) in an organic solvent. In a particularly preferred embodiment, the resulting compound of the formula (II) is then distilled. Or a2): prior to the work-up of the compound of the formula (III), optionally after distillation of some of the solvent, water is added to the reaction mass. Because of the acid which is liberated during the reaction of the compound of the formula (II) with a chlorinating agent, a low pH is established in the water phase during this operation. The water phase can then be separated again from the organic phase, or it is distilled off with the solvent without phase separation. In a particularly preferred embodiment, so little water is added that the amount just suffices to convert the hydrolysable byproducts present into low-volatility compounds. In this process variant, no water must therefore be separated off from the solvent or be removed from the solvent by azeotropic distillation. In a particularly preferred embodiment, the resulting compound of the formula (II) is then distilled.

Some compounds of the formulae (I) to (IV) containing asymmetric carbon atoms, as result of which the compounds can arise in optically active form. The formulae (I) to (IV) are intended to include all of these possible isomeric forms and mixtures thereof, for example racemates or E/Z-isomer mixtures.

Unless defined differently, the general terms used above and below have the meanings listed below:

unless defined otherwise, carbon-containing groups and compounds contain in each case 1 up to and including 8, preferably 1 up to and including 6, primarily 1 up to and including 4, in particular 1 or 2, carbon atoms.

Alkyl—as a group per se and as a structural element of other groups and compounds, such as of haloalkyl, arylalkyl or hydroxyalkyl—is, in each case with appropriate consideration of the number of carbon atoms present in the corresponding group or compound included from case to case, either straight-chain, such as, for example, methyl, ethyl, propyl, butyl, pentyl or hexyl, or branched, for example, isopropyl, isobutyl, sec-butyl, tert-butyl, isopentyl, neopentyl or isohexyl.

Alkenyl—as a group per se and as a structural element of other groups and compounds, such as of haloalkyl or arylalkenyl—is, in each case with appropriate consideration of the number of carbon atoms present in the corresponding group or compound included from case to case, either straight-chain, such as, for example, vinyl, 1-methylvinyl, allyl, 1-butenyl or 2-hexenyl, or branched, such as, for example, isopropenyl.

Alkynyl—as a group per se and as a structural element of other groups and compounds, such as of haloalkenyl—is, in each case with appropriate consideration of the number of carbon atoms present in the corresponding group or compound included from case to case, either straight-chain, such as, for example, propargyl, 2-butynyl or 5-hexynyl, or branched, such as, for example, 2-ethynylpropyl or 2-propargylisopropyl.

$C_3$–$C_6$Cycloalkyl is cyclopropyl, cyclobutyl, cyclopentyl or cyclohexyl, particularly cyclohexyl.

Aryl is phenyl or naphthyl, particularly phenyl.

Heteroaryl is understood as meaning a five- to seven-membered monocyclic aromatic ring which contains one to three heteroatoms chosen from the group consisting of N, O and S, particularly N and S, or a bicyclic heteroaryl which may, independently of one another, contain one or more heteroatoms, chosen from N, O and S either only in one ring, such as, for example, in quinolynyl, quinoxalynyl, indolynyl, benzothiophenyl or benzofuranyl, or else in both rings, such as, for example, in pteridynyl or purynyl. Preference is given to pyridyl, pyrimidynyl, thiazoyl and benzothiazolyl.

Halogen—as a group per se and as structural element of other groups and compounds, such as haloalkyl, haloalkenyl and haloalkynyl—is fluorine, chlorine, bromine or iodine, in particular fluorine, chlorine or bromine, particularly chlorine or bromine, very particularly chlorine.

Halogen-substituted carbon-containing groups and compounds, such as haloalkyl or haloalkenyl, can be partially halogenated or perhalogenated, where, in the case of multiple halogenation, the halogen substituents may be identical or different. Examples of haloalkyl—as a group per se and as structural element of other groups and compounds, such as of haloalkenyl—are methyl mono- to trisubstituted by fluorine, chlorine and/or bromine, such as $CHF_2$ or $CF_3$; ethyl mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl mono- to hepta substituted by fluorine, chlorine and/or bromine, such as $CH_2CHBrCH_2Br$, $CF_2CHFCF_3$, $CH_2CF_2CF_3$ or $CH(CF_3)_2$; and butyl or one of its isomers mono- to nonasubstituted by fluorine, chlorine and/or bromine, such as $CF(CF_3)CHFCF_3$ or $CH_2(CF_2)_2CF_3$. Haloalkenyl is e.g. $CH_2CH=CHCl$, $CH_2CH=CCl_2$, $CH_2CF=CF_2$ or $CH_2CH=CHCH_2Br$.

A leaving group X is understood above and below as meaning all suitable cleavable groups customary in chemical reactions, as are known to the person skilled in the art; particularly halogens, such as fluorine, chlorine, bromine, iodine, —O—C(=O)—A, —O—P(=O)(—A)$_2$, —O—Si$(C_1-C_8alkyl)_3$, —O—$(C_1-C_8alkyl)$, —O—aryl, —O—S$(=O)_2A$, —S—P(=O)(—A)$_2$, —S—P(=S)(—A)$_2$, —S—$(C_1-C_8alkyl)$, —S-aryl, —S(=O)A, —S(=O)$_2$A, or —O—C(=O)—A, in which A is optionally substituted $C_1-C_8$alkyl, $C_2-C_8$alkenyl, $C_2-C_8$alkynyl, optionally substituted aryl, optionally substituted benzyl, $C_1-C_8$alkoxy or di-($C_1-C_8$alkyl)amine, in which the alkyl groups are independent of one another; $NO_3$, $NO_2$, or sulphate, sulphite, phosphate, phosphite, carboxylate, imino esters, $N_2$ or carbamate.

Some compounds of the formulae (I) to (IV) may be present as tautomers. These compounds are therefore above and below to be understood as also meaning corresponding tautomers, even if the latter are not specifically mentioned in each case.

Compounds of the formulae (I) to (IV) which have at least one basic centre can form, for example, acid addition salts. These are formed, for example, with strong inorganic acids, such as mineral acids, e.g. perchloric acid, sulphuric acid, nitric acid, nitrous acid, a phosphoric acid or a hydrohalic acid, with strong organic carboxylic acids, such as optionally e.g. halogen-substituted $C_1-C_4$alkanecarboxylic acids e.g. acetic acid, such as optionally unsaturated dicarboxylic acids, e.g. oxalic acid, malonic acid , e.g. ascorbic acid, lactic acid, fumaric acid or phthalic acid, such as hydroxycarboxylic acids, e.g. ascorbic acid lactic acid, malic acid, tartaric acid or citric acid, or such as benzoic acid, or with organic sulphonic acids, such as optionally, e.g. halogen-substituted $C_1-C_4$alkane- or arylsulphonic acids, e.g. methane- or p-toluenesulphonic acid. In addition, compounds of the formulae (I) to (IV) with at least one acid group can form salts with bases. Suitable salts with bases are, for example, metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethylpropylamine, or a mono-, di- or trihydroxy-lower alkylamine, e.g. mono-, di- or triethanolamine. Furthermore, in some instances, corresponding internal salts may be formed. The compounds of the formulae (I) to (IV) are to be understood above and below as meaning both the compounds of the formulae (I) to (IV) in free form and also the corresponding salts. The corresponding statement applies to tautomers of the compounds of the formulae (I) to (IV) and salts thereof. In the case of the compounds of the formulae (I) and (III), preference is generally given in each case to a process for the preparation of the free form.

Within the scope of the invention, preference is given to (1) a process for the preparation of a compound of the formula (I) in which $R_1$ and $R_2$ in the compounds of the formulae (I) and (IV) are either, independently of one another, hydrogen or $C_1-C_4$alkyl, or together are a two- or three-membered alkylene bridge which optionally contains a heteroatom from the group consisting of $NR_5$, O and S, and $R_5$ is H or $C_1-C_4$alkyl;

particularly hydrogen or together a two- or three-membered alkylene bridge which optionally contains a heteroatom from the group consisting of $NR_5$ and O, and $R_5$ is $C_1-C_4$alkyl;

in particular $R_1$ and $R_2$ together are —$CH_2$—O—$CH_2$—, —$CH_2$—$CH_2$—$CH_2$—or —$CH_2$—$CH_2$—;

(2) a process according to position (1) above for the preparation of a compound of the formula (I) in which Q is N;

(3) a process according to positions (1) and (2) above for the preparation of a compound of the formula (I) in which Y is $NO_2$;

(4) a process according to positions (1 ) to (3) above for the preparation of a compound of the formula (I) in which Z is $NR_3$ and $R_3$is H or $C_1-C_4$alkyl;

(5) a process according to positions (1) to (4) above, in which, in the process stage a), the reaction temperature is in the range from –30° C. up to the boiling point of the solvent; particularly from –20° C. to +60° C.; in particular between +40° C. and +60° C., likewise preferably at +10° C. to +30° C., (6) a process according to positions (1) to (5) above, in which X in the compound of the formula (II) is halogen, such as fluorine, chlorine, bromine, iodine, —O—C(=O)—A, —O—P(=O)(—A)$_2$, —O—S$(=O)_2A$, —S—P(=O)(—A)$_2$, —S—P(=S)(—A)$_2$, —S(=O)A, or —S(=O)$_2$A, in which A is optionally substituted $C_1-C_8$alkyl, $C_2-C_8$alkenyl, $C_2-C_8$alkynyl, optionally substituted aryl, optionally substituted benzyl, $C_1-C_8$alkoxy or di-($C_1-C_8$alkyl)amine, in which the alkyl groups are independent of one another; particularly in which X is chlorine, bromine or iodine; in particular chlorine or bromine; very particularly preferably in which X is chlorine;

(7) a process according to positions (1) to (6) above, in which the water phase during the work-up of the reaction mixture of the compound of the formula (III) has a pH of less than 4; preferably less than 2; in particular less than 1.

(8) a process according to positions (1) to (7) above,- in which the extraction of the compound of the formula (III) in work-up variant a1) is carried out in aqueous hydrochloric, hydrobromic or hydroiodic acid, phosphoric acid, sulphuric acid, nitric acid or perchloric acid; aqueous hydrochloric acid with a concentration of from. 10 to 50% by weight, particularly 30 to 40% by weight, in particular 37% by weight, is particularly suitable. It is also preferred to use a hydrohalic acid whose anion corresponds to the group W of the compound of the formula (III);

(9) a process according to positions (1) to (7) in which, in the case of work-up variant a2), up to 500 mol %, particularly 100 mol %, preferably up to 30 mol %, of water, based on the compound of the formula (II) used; very particularly up to 20 mol % of water, based on the compound of the formula (II) used; particularly preferably up to 10 mol % of water, based on the compound of the formula (II) are added to the reaction mixture.

(10) a process according to positions (1) to (9) above, in which W in the compound of the formula (III) is chlorine;

(11) a process according to positions (1) to (10) above for the preparation of thiamethoxam, known from WO 98/32747; and of Ti-435 (clothianidin), known from EP-A-446913.

Process Step a)

The reaction of process step a), described above and below, is, where necessary, carried out in a sealed vessel, under pressure, in an inert-gas atmosphere and/or under anhydrous conditions. Particularly advantageous reaction conditions are given in the examples.

Suitable chlorinating agents are, in particular, chlorine, $POCl_3$, $PCl_3$, $PCl_5$ or $SO_2Cl_2$; preferably chlorine or $SO_2Cl_2$, very particularly a mixture of chlorine and $SO_2Cl_2$ or of chlorine and $SO_2$.

The reactants can in each case be reacted with one another as they are, i.e. without the addition of a solvent or diluent, e.g. in the melt. However, in most cases the addition of an inert solvent or diluent which is aprotic under the reaction conditions, or a mixture thereof, is advantageous. Examples of such solvents or diluents which may be mentioned are: aromatic, aliphatic and alicyclic hydrocarbons and halogenated hydrocarbons, such as benzene, toluene, xylene, mesitylene, tetralin, chlorobenzene, dichlorobenzene, bromobenzene, nitrobenzene, nitromethane, nitroethane, petroleum ether, hexane, cyclohexane; dichloromethane, trichloromethane, tetrachloromethane, 1,2-dichloroethane, 1,1,1-trichloroethane, 1,1,2,2-tetrachloroethane or tetrachloroethene; ethers, such as diethyl ether, dipropyl ether, diisopropyl ether, dibutyl ether, tert-butyl methyl ether, ethylene glycol dimethyl ether, dimethoxy diethyl ether, tetrahydrofuran or dioxane; amides, such as N,N-dimethylformamide, N,N-diethylformamide, N,N-dimethylacetamide, N-methylpyrrolidone or hexamethylphosphoramide; nitrites, such as acetonitrile or propionitrile; and sulphoxides, such as dimethyl sulphoxide; nitro compounds, such as nitromethane or nitrobenzene; or mixtures of such solvents.

Particularly preferred solvents are water-immiscible, apolar-aprotic solvents, such as halogenated hydrocarbons, such as halogenated alkanes and halogenated aromatics, such as dichloromethane, chloroform, tetrachloromethane, 1,2-dichloroethane, 1,1,1-trichloroethane, 1,2,3-trichloropropane, 1,1,2,2-tetrachloroethane, 1,2-dichloroethene, 1-chloropropane, chlorobenzene or 1,2-dichlorobenzene; or mixtures of such solvents. In addition, however, polar-aprotic solvents are also suitable; for example nitromethane or nitrobenzene; carbonitriles, such as acetonitrile, propionitrile or butyronitrile; carboxamides, such as formamide, N-methylformamide, N,N-dimethylformamide, N-methylacetamide, N,N-dimethylacetamide or 1-methylpyrrolidin-2-one; sulphoxides, such as dimethyl sulphoxide; sulpholane; hexamethylphosphoramide; 1,3-dimethylimidazolidin-2-one; a urea derivative, such as tetramethylurea; or mixtures of such solvents.

If the reaction according to precess stage a) is carried out in a water-miscible solvent, for the extraction with acid according to variant a1), a further solvent must be added which is immiscible with water and is inert towards acid. Suitable solvents for the purpose are, inter alia, particularly the water-immiscible solvents given above as preferred, and also aromatic solvents, such as, for example, benzene, toluene or xylene.

The extraction is preferably followed by a further purification step, for example by distillation or crystallization, of the pre-purified product of the formula (III).

It has been found that the non-cyclized byproducts and the compounds without basic nitrogen groups remain in the solvent phase and can be separated off with the solvent. In this connection, the extraction can be carried out batchwise or else continuously in an extraction column in countercurrent. The back-extraction of the product of the formula (III) from the aqueous phase is carried out, for example, with an inert, water-immiscible solvent. The back-extraction can also be carried out batchwise or continuously. The solvent is consequently distilled off under reduced pressure, and the product melt which remains is either used directly for subsequent synthesis stages, or, if desired, further purification operations, for example by distillation, are then carried out.

In the case of work-up variant a2), the reaction mixture which forms during the synthesis of the compound of the formula (III) is preferably admixed at 20–60° C. with water. In the case of this work-up variant too, the solvent is then advantageously distilled off under reduced pressure, and the product melt which remains is either used directly for subsequent synthesis stages, or after-treated by further purification operations, such as, for example, overhead distillation.

Process Step b)

The reactants can in each case be reacted with one another as they are, i.e. without the addition of a solvent or diluent, e.g. in the melt. However, in most cases, the addition of an inert solvent or diluent or a mixture thereof is advantageous. Examples of such solvents or diluents are: aromatic, aliphatic and alicyclic hydrocarbons and halogenated hydrocarbons, such as benzene toluene, xylene, mesitylene, tetralin, chlorobenzene, dichlorobenzene, bromobenzene, nitrobenzene, nitromethane, petroleum ether, hexane, cyclohexane, dichloromethane, trichloromethane, tetrachloromethane, dichloroethane, trichloroethene or tetrachloroethene; esters such as ethyl acetate, methyl acetate, dimethyl carbonate, diethyl carbonate, ethoxyethyl acetate, methoxyethyl acetate, ethyl formate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxy diethyl ether, tetrahydrofuran or dioxane; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoramide; nitrites, such as acetonitrile or propionitrile; and sulphoxides, such as dimethyl sulphoxide; or mixtures of such solvents. If the respective reaction is carried out in the presence of a base, bases used in excess, such as triethylamine, pyridine, N-methylmorpholine or N,N-diethylaniline, can also serve as solvents or diluents. Suitable solvents are in each case given in the examples. The addition of catalysts, such as, for example, phase transfer catalysts, is also advantageous.

The reaction is preferably carried out at a temperature of approximately 0° C. to approximately +180° C., particularly at about +10° C. to about +80° C., in many cases between room temperature and the reflex temperature of the solvent. In a particularly preferred embodiment of process step b), a compound of the formula (IV) is reacted at 0° C. to 120° C., particularly at 20° C. to 80° C., preferably at 30° C. to 70° C., in an ester, particularly in dimethyl carbonate, and preferably in the presence of a base, particularly $K_2CO_3$.

The reaction is preferably carried out at atmospheric pressure. The reaction time is not critical; preference is given to a reaction time of from 0.1 to 48 hours, particularly 0.5 to 12 hours. The product is isolated using customary methods, for example by filtration, crystallization, distillation or chromatography or any suitable combination of such methods. The yields achieved are usually good. A yield of 80% of the theoretical value can often be attained. Preferred conditions under which the reaction is carried out are given in the examples.

Salts of compounds of the formulae (I) to (IV) can be prepared in a manner known per se. Thus, for example, acid addition salts are obtained by treatment with a suitable acid or a suitable ion exchanger reagent, and salts with bases by treatment with a suitable base or a suitable ion exchanger reagent.

Salts of compounds of the formulae (I) to (IV) can be converted into the free compounds of the formulae (I) to (IV) in a customary manner, acid addition salts e.g. by treatment with a suitable basic agent or a suitable ion exchanger resin, and salts with bases e.g. by treatment with a suitable acid or a suitable ion exchanger reagent.

Salts of compounds of the formulae (I) to (IV) can be converted into other salts of compounds of the formulae (I) to (IV) in a manner known per se, acid addition salts, for example, into other acid addition salts, e.g. by treatment of a salt of an inorganic acid, such as a hydrochloride, with a suitable metal salt, such as a sodium, barium or silver salt, an acid, e.g. with silver acetate, in a suitable solvent in which an inorganic salt forms, e.g. silver chloride, is insoluble and therefore precipitates out from the reaction mixture.

Depending on the procedure and reaction conditions, the compounds of the formulae (I) to (IV) having salt-forming properties can be obtained in free form or in the form of salts.

The compounds of the formulae (I) to (IV) and in each case optionally their tautomers, in each case in free form or in salt form, may be in, the form of one of the possible isomers or as a mixture thereof, e.g. depending on the number, absolute and relative configuration of asymmetric carbon atoms arising within the molecule and/or depending on the configuration of nonaromatic double bonds arising within the molecule, as pure isomers, such as antipodes and/or diastereomers, or as isomer mixtures, such as enantiomer mixtures, e.g. racemates, diastereomer mixtures or racemate mixtures; the invention relates both to the pure isomers and also all possible isomer mixtures and is to be understood accordingly above and below even if stereochemical details are not specifically mentioned in each case.

Diastereomer mixtures and racemate mixtures of compounds of the formulae (I) to (IV) or salts thereof obtainable according to the process—depending on the choice of starting materials and procedures—or otherwise can be separated into the pure diastereomers or racemates on the basis of the physicochemical differences of the constituents in a known manner, for example by fractional crystallization, distillation and/or chromatography.

Enantiomer mixtures obtainable accordingly, such as racemates, can be split into the optical antipodes by known methods, for example by recrystallization from an optically active solvent, by chromatography over chiral adsorbents, e.g. high-pressure liquid chromatography (HPLC) over acetylcellulose, with the help of suitable microorganisms, by cleavage with specific, immobilized enzymes, via the formation of inclusion compounds, e.g. using chiral crown ethers, where only one enantiomer is complexed or by conversion into diastereomeric salts, e.g., by reacting a basic end-substance racemate with an optically active acid, such as carboxylic acid, e.g. camphoric acid, tartaric acid or malic acid, or sulphonic acid, e.g. camphorsulphonic acid, and separation of the diastereomer mixture obtained in this way, e.g. based on their different solubilities by fractional crystallization, into the diastereomers from which the desire enantiomer can be liberated by the action of suitable, e.g. basic, agents.

Apart from being obtained by separating corresponding isomer mixtures, it is also possible to obtain pure diastereomers or enantiomers according to the invention by generally known methods of diastereoselective or enantioselective synthesis, e.g. by carrying out the process according to the invention with starting materials with appropriately suitable stereochemistry.

The compounds of the formulae (I) to (IV) and salts thereof can also be obtained in the form of their hydrates and/or include other solvents used, for example, optionally for the crystallization of compounds present in solid form.

The invention relates to all those embodiments of the process according to which a compound obtainable at any stage of the process as starting material or intermediate, product, and all or some of the missing steps are carried out, or a starting material is used in the form of a derivative or salt and/or its racemates or antipodes or, in particular, forms under the reaction conditions.

Compounds of the formulae (I), (III) and (IV) obtainable in accordance with the process or otherwise can be converted into other corresponding compounds in a manner known per se.

In the processes of the present invention, preference is given to those using starting materials and intermediates, in each case in free form or in salt form, which lead to the compounds of the formula (I) described at the outset as particularly valuable, or salts thereof.

The present invention further provides the process for the preparation of a compound of the formula (III) from a compound of the formula (II) according to process step a) as described above.

The invention relates, in particular, to the preparation processes described in the examples.

The compounds of the formulae (II) and (IV) are known for example a intermediates for the preparation of pesticides, or they can be prepared by processes known per se.

PREPARATION EXAMPLES

EXAMPLE H1

Preparation of 3-chiorothiazol-5-ylmethyl)-5-methyl-4-nitrolmino-perhydro-1,3,5-oxadiazine H1a) 2-Chloro-5-chloromethylthiazole 40 g of an intermediate fraction from the distillation of the preliminary experiment, comprising 31.4 g of 2-chloro-5-chloromethylthiazole and 8.9 g of 2-chloro-3-thiocyanato-1-propene are introduced into 160 g of chlorobenzene, heated to 110° C. and stirred for one hour at 110° C. (conversion of 2-chloro-3-thiocyanato-1 -propene in 2-chloro-3-isothiocyanato-1-propene). The reaction mixture is cooled to 45–50° C. and supplemented with 125.3 g of fresh 2-chloro-3-isothiocyanato-1-propene and 100 g of chlorobenzene. At 45–50° C., 139 g of sulphuryl chloride are metered in over 5 hours and then the mixture is further stirred for one hour at 45–50° C. The pressure is then adjusted to 120 mbar and the temperature to 50–55° C. and the reaction is completed by stirring for one hour and then all of the solvent is distilled off from the reaction mass. An intermediate fraction of 40 g is then taken, which is reintroduced in the subsequent batch. Fractional distillation of the crude product at 115° C./5–10 mbar gives 124.4 g of 2-chloro-5-chloromethylthiazole with a content of 94.5%, which corresponds to a yield of 74.6% of theory, based on freshly used 2-chloro-3-isothiocyanato-1-propene.

H1b) 3-(2-Chlorothiazol-5-ylmethyl)-5-methyl-4-nitroiminoperhydro-1,3,5-oxadiazine A sulphonation flask is charged with 184 g of 3-methyl-4-nitroiminoperhydro-1,3,5-oxadiazine 100% in 400 g of dimethyl carbonate, and 168 g of 2-chloro-5-chloromethylthiazole 100%, which is prepared according to the method described in Example H1a), are added. This mixture is heated to 65° C. With stirring at 60° C. to 70° C., a mixture consisting of 350 g of dimethyl carbonate, 4 g of tetramethylammonium hydroxide pentahydrate and 242 g of potassium carbonate powder is metered in over the course of 60 minutes. The reaction mixture is stirred until the conversion of 2-chloro-5-chloromethylthiazole is more than 99% (LC check).

The reaction mixture is then cooled, and 600 g of water are added thereto. Using approximately 260 g of hydrochloric acid 32%, the pH is adjusted to 6.5, and left to stand to allow phase separation, and the organic phase is separated off. The organic phase is concentrated by evaporation at 60° C. under reduced pressure to a final weight of 600 g. The mixture is slowly cooled to 0–5° C. and kept at this temperature for one hour. The suspension which forms is then filtered and the resulting solid product is dried. The content of the resulting product is 97.5–98.5%, and the colour is dark brown. The yield is 70% of theory.

EXAMPLE H2

Preparation 3-(2-chlorothiazol-5-ylmethyl)-5-methyl-4-nitroiminoperhydro-1,3,5-oxadiazine H2a): 2-Chloro-5-chloromethylthiazole 40 g of an intermediate fraction from the distillation of the preliminary experiment, comprising 31.4 g of 2-chloro-5-chloromethylthiazole and 8.9 g of 2-chloro-3-thiocyanato-1-propene are introduced into 160 g of chlorobenzene, heated to 110° C. and stirred for one hour at 110° C. The reaction mixture is cooled to 45–50° C. and supplemented With 125.3 g of fresh 2-chloro-3-isothiocyanato-1-propene and 100 g of chlorobenzene. At 45–50° C., 139 g of sulphuryl chloride are metered in over 5 hours and then the mixture is further stirred for one hour at 45–50° C. The pressure is then adjusted to 120 mbar and the temperature to 50–55° C., and the reaction is completed by stirring under these conditions for one hour. Half of the solvent is then distilled off at 60–65° C./20–30 mbar from the reaction mass.: At 50–55° C., 7 g of water are added to the reaction mass, and the mixture is further stirred at this temperature for one hour. Then, at 60–65° C./20–30 mbar, the residual solvent is distilled off, then 40 g of intermediate fraction and finally, at 115° C./5–10 mbar of the crude product. This gives 121 g of 2-chloro-5-chloromethylthiazole with a content of 98%, which corresponds to a yield of 70.5% of theory, based on 2-chloro-3-isothiocyanato-1-propene, respectively to a yield of 75% of theorywith regard,to freshly used 2-chloro-3-isothiocyanato-1-propene.

H2b): 3-(2-Chlorothiazol-5-ylmethyl)-5-methyl-4-nitroiminoperhydro-1,3,5-oxadiazine The preparation of the final product is carried out in the same way as described in Example H1b), using 2-chloro-5-chloromethylthiazole which has been prepared according to the method described in Example H2a). The content of the resulting product is 98–99%, and the colour is light pale beige. The yield is 74–75% of theory.

EXAMPLE H3

Preparation of 3-(2-chlorothiazol-5-ylmethyl)-5-methyl-4-nitroiminoperhydro-1,3,5-oxadiazine H3a): 2-Chloro-5-chloromethylthiazole 87.7 g of 2-Chloro-3-isothiocyanato-1-propene are introduced into 100 ml of acetonitrile at 20° C., and 8.9 g of sulphuryl chloride (0.05 mol) are added to the reaction mixture. 41.5 g of chlorine are then introduced over 2 hours until excess starting material can no longer be detected and the reaction solution is stirred for a further hour at 40° C. and then cooled to room temperature. Hydrogen chloride gas is stripped off under reduced pressure and the acetonitrile is distilled off. This gives 112 g of 2-chloro-5-chloromethylthiazole with a content of 91% yield: 84% of theory, based on 2-chloro-3-isothiocyanato-1-propene.

H3b): 3-(2-Chlorothiazol-5-ylmethyl)-5-methyl-4-nitrominoperhydro-1,3,5-oxadiazine The preparation of the final product is carried out in the same way as described in Example H1b), using 2-chloro-5-chloromethylthiazole which has been prepared according to the method described in Example H3a). The content of the resulting product is 92–94%, and the colour is dark brown. The yield is 50–55% of theory.

EXAMPLE H4

Preparation of 3-(2-chlorothiazol-5-ylmethyl)-5-methyl-4-nitroiminoperhydro-1,3,5-oxadiazine H4a): 2-Chloro-5-chloromethylthiazole 87.7 g of 2-chloro-3-isothiocyanato-1-propene are introduced at 20° C. into 100 ml of acetonitrile, and 8.9 g of sulphuryl chloride (0.05 mol) are added to the reaction mixture. 41.5 g of chlorine are then introduced over the course of 2 hours until excess starting material can no longer be detected, and the reaction solution is stirred for one hour at 40° C. and then acetonitrile and HCl are largely distilled off up to a final reduced pressure of 20 mbar. 200 ml of toluene are added to the crude melt which remains, and the toluenic product solution is extracted using a total of 250 g of hydrochloric acid 37% in 4 portions. The aqueous extracts containing the 2-chloro-5-chloromethylthiazole hydrochloride are purified and, after the addition of 200 ml of toluene, partially neutralized with 250 g of sodium hydroxide solution 30%. Toluene and then 2-chloro-5-chloromethylthiazol are successively distilled out of the toluenic phase up to a final reduced pressure of 5–10 mbar at the head. This gives 86 g of 2-chloro-5-chloromethylthiazole with a content of 98%. Yield: 76% of theory based on 2-chloro-3-isothiocyanato-1-propene.

H4b) 3-(2-Chlorothiazol-5-ylmethyl)-5-methyl-4-nitroiminoperhydro-1,3,5-oxadiazine The preparation of the final product is carried out in the same way as described in Example H1b), using 2-chloro-5- chloromethylthiazole which has been prepared according to the method described in Example H4a). The content of the resulting product is 98–99%, and the colour is beige. The yield is 76–77% of theory.

EXAMPLE H5

Preparation of 3(2-cholorothiazol-5-ylmethyl)-5-methyl-4-nitroiminoperhydro-1,3,5-oxadiazine H5a) 2-Chloro-5-chloromethylthiazole 139 g of sulphuryl chloride are metered into a solution 133.6 g of 2-chloro-3-isothiocyanato-1propene in 260 g of chlorobenzene at 45–50° C. over 5. hours. The reaction mixture is then stirred for a further hour at 45–50° C. The pressure is then adjusted to 120 mbar, and the temperature to 50–55° C., and the mixture is stirred for one hour under these conditions to remove the gas. The reaction mixture is cooled to 20–25° C. and extracted with a total of 460 g of hydrochloric acid 37% in four portions. The water phase is separated off each time. The combined water phases are diluted with 580 g of water, and the product is back-extracted with a total of 170 g of chlorobenzene in two portions. The solvent is then distilled off at 60–65° C./20–30 mbar, and the crude product is distilled off at 115° C./5–10 mbar. This gives 117.1 g of 2-chloro-5-chloromethylthiazole with a content of 99%, which corresponds to a yield of 69% of theory based on 2-chloro-3-isothiocyanato1-propene.

H5b): 3-(2-Chlorothiazol-5-ylmethyl)-5-methyl-4-nitroiminoperhydro-1,3,5-oxadiazine The preparation of the final product is carried out in the same way as described in Example H1b), using 2-chloro-5-chloromethylthiazole which has been prepared according to the method described in Example H5a). The content of the resulting product is 98–99%, and the colour is pale beige. The yield is 77–78% of theory.

EXAMPLE H6

Preparation of 3-(2-chlorothiazol-5-ylmethyl)-5-methyl-4-nitroiminoperhydro-1,3,5-oxadiazine H6a) 2-Chloro-5-chloromethylthiazole 139 g of sulphuryl chloride are metered into a solution of 133.6 g of 2-chloro-3-isothiocyanato-1-propene in 250 g of 1,2-dichlorethane at 45–50° C. over 4 hours. The reaction mixture is then stirred for a further 2 hours at 45–50° C. The reaction mixture is cooled to 20–25° C. and extracted with a total of 460 g of hydrochloric acid 37% in four portions. The water phase is separated off each time. The combined water phases are diluted with 580 g of water, and the product is back-extracted with a total of 170 g of 1,2-dichloroethane in two portions. The solvent is then distilled off at 60–65° C./20–30 mbar, and the crude product is distilled off at 115° C./5–10 mbar. This gives 119 g of 2-chloro-5-chloromethylthiazole with a content of 99%, which corresponds to a yield of 70% of theory, based on 2-chloro-3-isothiocyanato-1-propene.

H6b): 3-(2-Chlorothiazol-5-ylmethyl)-5-methyl-4-nitroiminoperhydro-1,3,5-oxadiazine The preparation of the final product is carried out in the same way as described in Example 1b), using 2-chloro-5-chloromethylthiazole which has been prepared according to the method described in Example H6a). The content of the resulting product is 98–99%, and the colour is pale beige. The yield is 77.–79% of theory.

What is claimed is:
1. A process for the preparation of a compound of the formula

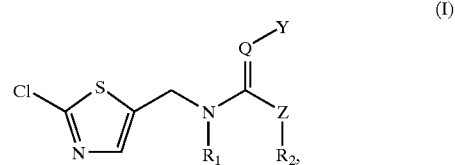

(I)

and optionally its E/Z-isomers, E/Z-isomer mixtures and/or tautomers, in each case in free form or in salt form, in which Q is CH or N;
Y is $NO_2$ or CN;
Z is $CHR_3$, O, $NR_3$ or S;
$R_1$ and $R_2$ are either, independently of one another, hydrogen, unsubstituted or $R_4$-substituted $C_1$–$C_8$alkyl, or together are an alkylene bridge having two or three carbon atoms which optionally comprises a heteroatom chosen from the group consisting of $NR_5$, O and S,
$R_3$ is H or unsubstituted or $R_4$-substituted $C_1$–$C_{12}$alkyl,
$R_4$ is unsubstituted or substituted aryl or heteroaryl, and
$R_4$ is H or $C_1$–$C_{12}$alkyl; in which a) a compound of the formula

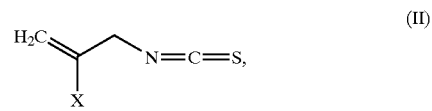

(II)

which is known or can be prepared by known methods, and in which X is a leaving group, is reacted with a halogenating agent to give a compound of the formula

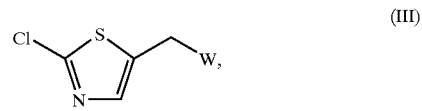

(III)

In which W is a halogen atom, or optionally a tautomer, in each case in free form or in salt form; and in which the work-up of the compound of formula (III) involves an extraction of the compound of formula (III) with hydrochloric acid of concentration between 10 and 50% by weight; and b) the resulting compound of the formula (III) is reacted with a compound of the formula

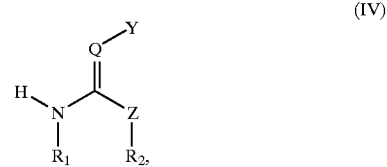

(IV)

in which $R_1$, $R_2$, Y, Z and Q have the meanings given above for the compound of the formula (I);
wherein the preparation of the compound of the formula (III) according to process stage a) involves a purification step in which the crude product which has formed is treated with water in the acidic pH range.

2. A process according to claim 1, in which the work-up of the compound of the formula (III) in process step a) involves the addition of up to 500 mol% of water, based on the compound of the formula (II) used, to the reaction mass.

3. A process according to claim 1, in which the process step a) is carried out in an apolar-aprotic solvent.

4. A process for the preparation of a compound of the formula

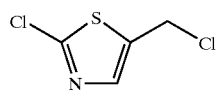

(III), or optionally a tautomer, in each case in free form or in salt form, in which a compound of the formula

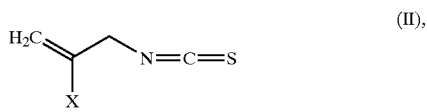

(II), or optionally a tautomer, in each case in free form or in salt form, in which X is a leaving group, is reacted with a chlorinating agent, wherein the preparation of the compound of the formula (III) involves a purification step in which the reaction mass which has formed is treated with water in the acidic pH range, and in which the work-up of the compound of formula (III) involves an extraction of the compound of formula (III) with hydrochloric acid of concentration between 10 and 50% by weight.

* * * * *

UNITED STATES PATENT AND TRADEMARK OFFICE
CERTIFICATE OF CORRECTION

PATENT NO. : 6,861,522 B2
DATED : March 1, 2005
INVENTOR(S) : Rapold et al.

It is certified that error appears in the above-identified patent and that said Letters Patent is hereby corrected as shown below:

Column 14,
Line 26, should read as follows -- R5 is H or C1-C12alkyl; in which --

Signed and Sealed this

Seventeenth Day of May, 2005

JON W. DUDAS
*Director of the United States Patent and Trademark Office*